(12) United States Patent
Naguib et al.

(10) Patent No.: US 10,052,395 B1
(45) Date of Patent: Aug. 21, 2018

(54) [$^{18}$F] FLUORIDE CRYPTATE COMPLEXES FOR RADIOLABELING FLUORINATIONS

(71) Applicants: Yousry Naguib, Arcadia, CA (US); Ashraf Naguib, Arcadia, CA (US); Ahmed Naguib, Arcadia, CA (US)

(72) Inventors: Yousry Naguib, Arcadia, CA (US); Ashraf Naguib, Arcadia, CA (US); Ahmed Naguib, Arcadia, CA (US)

( * ) Notice: Subject to any disclaimer, the term of this patent is extended or adjusted under 35 U.S.C. 154(b) by 0 days.

(21) Appl. No.: 15/731,330

(22) Filed: May 30, 2017

(51) Int. Cl.
*C07D 498/08* (2006.01)
*A61K 51/04* (2006.01)
*C07B 59/00* (2006.01)
*G21G 4/08* (2006.01)

(52) U.S. Cl.
CPC .......... *A61K 51/041* (2013.01); *C07B 59/002* (2013.01); *C07D 498/08* (2013.01); *G21G 4/08* (2013.01)

(58) Field of Classification Search
None
See application file for complete search history.

(56) References Cited

U.S. PATENT DOCUMENTS

| | | | | |
|---|---|---|---|---|
| 5,264,570 A | * | 11/1993 | Johnson | C07H 5/02 536/122 |
| 2008/0274046 A1 | * | 11/2008 | Prenant | A61K 51/088 424/1.49 |
| 2011/0059014 A1 | * | 3/2011 | Namavari | C07H 19/16 424/1.73 |

OTHER PUBLICATIONS

Lambert. Organic Structural Spectroscopy, 1998, pp. 287-289. (Year: 1998).*
Naguib. Molecules, 2009, 14, 3600-3609. (Year: 2009).*
Lambert. Organic Structural Spectroscopy, 1998, 278-79.*

* cited by examiner

*Primary Examiner* — Noble E Jarrell

(57) ABSTRACT

The present invention claims UV detectable ($\lambda$>210 nm) potassium [$^{18}$F]fluoride diaryl- and aryl-fused [2.2.2] cryptate complexes suitable for performing radio-labeling reactions to generate [$^{18}$F] fluorinated species.

1 Claim, No Drawings

[$^{18}$F] FLUORIDE CRYPTATE COMPLEXES FOR RADIOLABELING FLUORINATIONS

CROSS-REFERENCE TO RELATED APPLICATION

The disclosure is a continuation of U.S. patent application Ser. No. 13/589,155, filed Aug. 19, 2012, which is incorporated herein by reference.

FIELD OF THE INVENTION

The present invention relates to [$^{18}$F]fluoride diaryl- and aryl-fused [2.2.2]cryptate complexes suitable for performing radio-labeling reactions to generate [$^{18}$F] fluorinated species for use as imaging agents.

A cryptand is a phase-transfer agent used to complex [$^{18}$F] fluoride anion to form [$^{18}$F] fluoride cryptate complexes and that a [$^{18}$F] fluorinated species defined herein comprises chemical or biological [$^{18}$F] fluorinated compounds.

BACKGROUND OF THE INVENTION

Positron Emission Tomography (PET) relies upon the use of positron emitting radiolabeled tracer molecules and computed tomography to examine metabolic processes or to detect targets within the living body of a patient or experimental animal. Once injected, the tracer is monitored with a positron camera or a tomograph detector array. This technology can be more sensitive than scanning techniques such as magnetic resonance imaging (MRI), ultrasound imaging, or X-ray imaging. Some of the major clinical applications for PET are oncology, neurology, and cardiology. Positron emitting compounds may be employed as markers and imaging agents because their presence and location are indicated by the annihilation of a nearby electron and the consequent emission of two oppositely oriented gamma rays. Gamma ray detectors can be used to detect the event and precisely determine its location. Tracer molecules used in PET imaging are generally prepared by replacement of a group or atom in an unlabeled tracer with a radioisotope containing group or atom or by joining the tracer to a radioisotope containing atom (e.g. by chelation). Some common positron-emitting radioisotopes commonly used are: fluorine-18 ($^{18}$F); carbon-11 ($^{11}$C); nitrogen-13 ($^{13}$N); and oxygen-15 ($^{15}$O). In addition, $^{64}$Cu has been appended to tracer molecules using copper chelation chemistry (Chen et al. Bioconjug. Chem. (2004) 15: 41-49).

$^{18}$F is a particularly desirable radioisotope for PET imaging since it has a longer half-life than $^{11}$C, $^{13}$N and $^{15}$O, readily forms covalent bonds, and has a short range beta+ emission that provides for high resolution in PET imaging.

Natural, stable fluorine is $^{19}$F. $^{18}$F has one less neutron for that number of protons, which is why it decays by positron emission.

$^{18}$F is a fluorine radioisotope which is an important source of positrons. It has a mass of 18.0009380 u and its half-life is 109.771 minutes. It decays by positron emission 97% of the time and electron capture 3% of the time. Both modes of decay yield stable oxygen-18 ($^{18}$O). $^{18}$F is an important isotope in the radiopharmaceutical industry. For example, it is synthesized into fluorodeoxyglucose (FDG) for use in positron emission tomography (PET scans). It is substituted for hydroxyl and used as a tracer in the scan. Its significance is due to both its short half-life and the emission of positrons when decaying.

In the radiopharmaceutical industry, the radioactive $^{18}$F must be made first as the fluoride anion ($^{18}$F$^-$) in the cyclotron. This may be accomplished by bombardment of neo-20 with deuterons, but usually is done by proton bombardment of $^{18}$O-enriched water, with high energy protons (typically ~18 MeV protons). This produces "carrier-free" dissolved $^{18}$F-fluoride ($^{18}$F$^-$) ions in the water. Fluorine-18 is often substituted for a hydroxyl group in a radiotracer parent molecule. PET tracers often are or include a molecule of biological interest (a "biomolecule").

Biomolecules developed for use in PET have been numerous. They can be small molecules as ubiquitous as water, ammonia and glucose or more complex molecules intended for specific targeting in the patient, including labeled amino acids, nucleosides and receptor ligands. Specific examples include, but not limited to, $^{18}$F labeled fluorodeoxyglucose, methionine, deoxythymidine, L-DOPA, raclopride and Flumazenil. (Fowler J. S. and Wolf A. P. (1982), and The synthesis of carbon-11, fluorine-18 and nitrogen-13 labeled radiotracers for biomedical applications. Nucl. Sci. Ser. Natl Acad. Sci. Natl Res. Council Monogr. 1982).

The 109.8 minute half-life of $^{18}$F makes rapid and automated chemistry necessary after this point. $^{18}$F-fluoride anion ($^{18}$F) is often converted to a form suitable as an agent in aliphatic nucleophilic displacements or aromatic substitution reactions. $^{18}$F may be combined with a metal ion complexing agent such as cryptand or a tetrabutyl ammonium salt, a triflate, or a positively charged counter ion (including H$^+$, K$^+$, Na$^+$, etc).

Fluorination agents may be used in an appropriate solvent or cosolvent, including without limitation water, methanol, ethanol, THF, dimethylformamide (DMF), formamide, dimethylacetamide (DMSO), DMA, dioxane, acetonitrile, and pyridine.

In nucleophilic radiofluorination, the first major step is drying the aqueous [$^{18}$F] fluoride which is commonly performed in the presence of a phase-transfer catalyst under azeotropic evaporation conditions (Coenen et al., J. Labelled Compd. Radiopharm., 1986, vol. 23, pgs. 455-467). The [$^{18}$F] fluoride that is solubilized or dissolved in the target water is often adsorbed on an anion exchange resin and eluted, for example, with a potassium carbonate solution (Schlyer et al., Appl. Radiat. Isot., 1990, vol. 40, pgs. 1-6). One cryptand that is available commercially is 4,7,13,16, 21,24-hexaoxa-1,10-diazabicyclo [8,8,8] hexacosan, with the tradename Kryptofix 222. Cryptand is a cage-like agent that has three ether ribs joining the nitrogens at each end. Alkali metals can be held very strongly inside the cage. The treatment with $^{18}$F$^-$ is suitably effected in the presence of a suitable organic solvent such as acetonitrile, dimethylformamide, dimethylsulphoxide, tetrahydrofuran, dioxan, 1,2 dimethoxyethane, sulpholane, N-methylpyrolidinineone, In nucleophilic fluorination reactions, anhydrous conditions are required to avoid the competing reaction with hydroxide. [Aigbirhio et al 1995 J. Fluor. Chem. 70 pp 279-87]. The removal of water from the fluoride ion is referred to as making "naked" fluoride ion. This is regarded in the prior art relating to nucleophilic fluoridation as a step necessary to increase the reactivity of fluoride as well as to avoid hydroxylated by-products resulting from the presence of water [Moughamir et al 1998 Tett. Letts. 39 pp 7305-6; and Handbook of Radiopharmaceuticals 2003 Welch & Redvanly eds. ch. 6 pp 195-227). The removal of water from the [$^{18}$F] Fluoride is referred to as making "naked" [$^{18}$F] Fluoride. This is regarded in the prior art relating to nucleophilic fluoridation as a step necessary to increase the reactivity of fluoride as well as to avoid hydroxylated by-products resulting from the presence of water (Moughamir et al 1998 Tett Letts; 39: 7305-6).

The use of the cryptand to sequester the potassium ions avoids ion-pairing between free potassium and fluoride ions, making the fluoride anion more reactive. For example, [(2.2.2-cryptand) K$^+$] $^{18}$F$^-$ is reacted with a protected mannose triflate; the fluoride anion displaces the triflate leaving group in an S$_N^2$ reaction, giving the protected fluorinated deoxyglucose. Base hydrolysis removes the acetyl protecting groups, giving the desired product $^{18}$FDG after removing the cryptand via ion-exchange (Fowler J S, Ido T (2002). "Initial and subsequent approach for the synthesis of $^{18}$FDG". *Semin Nucl Med* 32 (1): 6-12; and Yu, S (2006). "Review of $^{18}$F-FDG synthesis and quality control". *Biomedical Imaging and Intervention Journal* 2).

To improve the reactivity of fluoride ion for fluoridation reactions a cationic counterion is added prior to the removal of water. The counterion should possess sufficient solubility within the anhydrous reaction solvent to maintain the solubility of the fluoride ion. Therefore, counterions that have been used include large but soft metal ions such as rubidium or caesium, potassium complexed with a cryptand such as Kryptofix™, or tetraalkylammonium salts. A preferred counterion for fluoridation reactions is potassium complexed with a cryptand such as Kryptofix™, because of its good solubility in anhydrous solvents and enhanced fluoride reactivity.

Fluorodeoxyglucose ($^{18}$F) or fludeoxyglucose ($^{18}$F), commonly abbreviated $^{18}$F-FDG or FDG, is a radiopharmaceutical used in the medical imaging modality positron emission tomography (PET). Chemically, it is 2-deoxy-2-($^{18}$F) fluoro-D-glucose, a glucose analog, with the positron-emitting radioactive isotope fluorine-18 substituted for the normal hydroxyl group at the 2' position in the glucose molecule. Synthesis of the FDG itself is not considered to be part of this invention and only a basic description of a process is included here.

Production of $^{18}$F-labeled FDG is, by now, well known. Information can be found in: 1) Fowler et al., "2-Deoxy-2-[$^{18}$F]Fluoro-D-Glucose for Metabolic Studies: Current Status," Appl. Radiat. Isotopes, vol. 37, no. 8, pp. 663-668 (1986); 2) Hamacher et al., "Efficient Stereospecific Synthesis of No-Carrier-Added 2-[$^{18}$F]-Fluoro-2-Deoxy-D-Glucose Using Aminopolyether Supported Nucleophilic Substitution," J. Nucl. Med., vol. 27, pp. 235-238 1986; 3) Coenen et al., "Recommendation for Practical Production of [2-$^{18}$F] Fluoro-2-Deoxy-D-Glucose," Appl. Radiat. Isotopes, vol. 38, no. 8, pp. 605-610 (1987) (a good review); 4) Knust et al., "Synthesis of $^{18}$F-2-deoxy-2-fluoro-D-glucose and $^{18}$F-3-deoxy-3-fluoro-D-glucose with no-carrier-added $^{18}$F-fluoride," J. Radioanal. Nucl. Chem., vol. 132, no. 1, pp. 85-91 (1989); and 5) Hamacher et al., "Computer-aided Synthesis (CAS) of No-carrier-added 2-[$^{18}$F]Fluoro-2-Deoxy-D-Glucose: An Efficient Automated System for the Aminopolyether-supported Nucleophilic Fluorination," Appl. Radiat. Isotopes, vol. 41, no. 1, pp. 49-55 (1990). See also U.S. Pat. No. 6,567,492 to Kislelev al. (20 May 2003).

Several automatic processing systems capable of production of radiopharmaceuticals, such as $^{18}$F-labeled FDG, have also been described in: 1) U.S. Pat. No. 5,808,020 to Ferrieri et al. (15 Sep. 1998); 2) U.S. Pat. No. 6,599,484 to Zigler et al. (29 Jul. 2003); PCT pub. WO2004093652 by Buchanan et al. (2004 Nov. 4); and 3) German patent DE10320552 to Maeding et al. "Apparatus marking pharmaceutical substances with fluorine isotope, preparatory to positron-emission tomography, locates anion exchanger within measurement chamber" (2004 Nov. 25).

Clinical Use of $^{18}$F-FDG $^{18}$F-FDG, as a glucose analog, is taken up by high-glucose-using cells such as brain, kidney, and cancer cells, where phosphorylation prevents the glucose from being released again from the cell, once it has been absorbed. The 2' hydroxyl group (—OH) in normal glucose is needed for further glycolysis (metabolism of glucose by splitting it), but $^{18}$F-FDG is missing this 2' hydroxyl. Thus, in common with its sister molecule 2-deoxy-D-glucose, FDG cannot be further metabolized in cells. The $^{18}$F-FDG-6-phosphate formed when $^{18}$F-FDG enters the cell thus cannot move out of the cell before radioactive decay. As a result, the distribution of $^{18}$F-FDG is a good reflection of the distribution of glucose uptake and phosphorylation by cells in the body. After $^{18}$F-FDG decays radioactively, however, its 2'-fluorine is converted to $^{18}$O$^-$, and after picking up a proton H$^+$ from a hydronium ion in its aqueous environment, the molecule becomes glucose-6-phosphate labeled with harmless nonradioactive "heavy oxygen" in the hydroxyl at the 2' position. The new presence of a 2' hydroxyl now allows it to be metabolized normally in the same way as ordinary glucose, producing non-radioactive end-products.

After $^{18}$F-FDG is injected into a patient, a PET scanner can form images of the distribution of FDG around the body. The images can be assessed by a nuclear medicine physician or radiologist to provide diagnoses of various medical conditions.

In PET imaging, $^{18}$F-FDG can be used for the assessment of glucose metabolism in the heart, lungs, and the brain. It is also used for imaging tumors in oncology, where a static $^{18}$F-FDG PET scan is performed and the tumor $^{18}$F-FDG uptake is analyzed in terms of Standardized Uptake Value (SUV). $^{18}$F-FDG is taken up by cells, phosphorylated by hexokinase (whose mitochondrial form is greatly elevated in rapidly growing malignant tumours), and retained by tissues with high metabolic activity, such as most types of malignant tumours. As a result FDG-PET can be used for diagnosis, staging, and monitoring treatment of cancers, particularly in Hodgkin's disease, colorectal cancer, breast cancer, melanoma, lung cancer, and Alzheimer's disease.

Cryptands

Cryptands and other macrocyclic compounds such as crown ethers, spherands, cryptahemispherands, cavitands, calixarenes, resorcinorenes, cyclodextrines, porphyrines and others are well known. (Comprehensive Supramolecular Chemistry Vol. 1-10, Jean-Marie Lehn—Chairman of the Editorial Board, 1996 Elsevier Science Ltd.) Many of them are capable of forming stable complexes with ionic organic and inorganic molecules. Those properties make macrocyclic compounds candidates for various fields, for instance, catalysis, separations, sensors development and others. Cryptands (bicyclic macrocycles) have extremely high affinity to metal ions. The cryptand metal ion complexes are more stable than those formed by monocyclic ligands such as crown ethers (Izatt, R. M., et al., Chemical Reviews 91:1721-2085 (1991)). This high affinity of the cryptands to alkaline and alkaline earth metal ions in water makes them superior complexing agents for the processes where strong, fast and reversible metal ion binding is required. Examples of these processes include separation, preconcentration and detection of metal ions, analysis of radioactive isotopes, ion-exchange chromatography, phase-transfer catalysis, activation of anionic species and others.

Many strategies for the synthesis of macrocyclic compounds have been developed over the years (Comprehensive Supramolecular Chemistry Vol. 1-10, Jean-Marie Lehn—Chairman of the Editorial Board, 1996 Elsevier Science Ltd.; Krakowiak, K. E., et al., Israel Journal of Chemistry 32:3-13 (1992); Bradshaw, J S., et al., "Aza-Crown Macrocycles," The Chemistry of Heterocyclic Compounds, Vol. 51, ed. Taylor, E. C., Wiley, New York, 1993; Haoyun, A., et al., Chemical Reviews 92:543-572 (1992)).

The Cryptands may be synthesised as described in US20040267009 A1, Bernard Dietrich, Jean-Marie Lehn, Jean Guilhem and Claudine Pascard, Tetrehedron Letters, 1989, Vol. 30, No. 31, pp 4125-4128, Paul H. Smith et al, J. Org. Chem., 1993, 58, 7939-7941, Jonathan W. Steed et al, 2004, Journal of the American Chemical Society, 126, 12395-12402, Bing-guang Zhang et al, Chem. Comm., 2004, 2206-2207.

Cryptands are cavity containing macromolecules which form stable complexes with alkali metal ions. For a given cation, the stability constant is largest for the cation which fits best into the cavity of the ligand. Thus stability maxima are found for $Li[2.1.1]^+$, $Na[2.2.1]^+$, and $K[2.2.2]^+$ (Cox, B. G. Effects of substituents on the stability and kinetics of alkali metal cryptates in methanol. *Inorganica Chimica Acta*, 1981, 49, 153-158).

SUMMARY OF THE INVENTION

In one embodiment of the present invention novel $[^{18}F]$ fluoride diaryl- and aryl-fused [2.2.2]cryptate complexes suitable for radiolabeling fluorinations.

A further embodiment of the method in the present invention is wherein the di-substitutent in the di-substituted [2.2.2] cryptand is diaryl. Yet another embodiment of the invention is wherein the di-substituent in the disubstituted [2.2.2] cryptand is dibenzo. Yet another embodiment of the invention is wherein the di-substituent in the disubstituted [2.2.2] cryptand is dinaphtho. Yet, in a further embodiment of the present method the $[^{18}F]$ fluoride-complex is used to radiolabel a $[^{18}F]$ fluorinated species wherein the radiolabelled $[^{18}F]$ fluorinated species is used as an imaging agent in a patient.

Still another embodiment of the present invention discloses the imaging agent as being viewed within a patient by an imaging technique such as a positron emission tomography ("PET") scanner.

DETAILED DESCRIPTION OF THE INVENTION

The effect of substituents on macrocyclic molecules was first observed by Pedersen (Pedersen, C. J. *J. Am. Chem. Soc.* 1967, 89, 7017). Subsequently, many different moieties have been introduced into the macrocyclic backbone to modify the properties of the hosts, e.g., to increase rigidity and lipophilicity, (Marchand, A. P.; Huang, Z.; Chen, Z.; Hariprakasha, H. K.; Namboothiri, I. N. N.; Brodbelt, J. S.; Reyzer, M. L. *J. Heterocyclic Chem.* 2001, 38, 1361). The effect of increased rigidity introduced by the incorporated moiety can be interpreted in terms of preorganization. The principle of preorganization (Cram, D. J. in *From Design to Discovery* American Chemical Society, Washington D.C., 1991, p 9) states: "The more highly hosts and guests are organized for binding and low solvation prior to complexation, the more stable will be the complexes.

The topology, along with ring size determines the degree of preorganization of a specific structure for complexation. The general trend is that the two-dimensional structure develops into a three dimensional structure, wherein, for similar ring-size, the rigidity of the molecule increases. For example, rigidity increases along the series 18-crown-6, [2.2.2]-cryptand. Increasing rigidity in this way restricts the ability of the ligand to undergo conformational reorganization. Thus more rigid ligands are more highly "preorganized". Since the host must undergo conformational adjustment to provide a proper binding environment during the host-guest interaction. Thus, preorganization of a ligand, which is associated with its topology, rigidity and solvation, becomes important. For a specific guest, the more highly preorganized ligand requires less conformational change and thus pays minimal energy cost for conformational adjustment.

Increasing rigidity of the host the more highly preorganized host and the more highly host and guest are organized for binding the more stable the complexes will be.

In order to attain high, yet selective binding of a potassium ion chelator some rigidity in the system such as the ionophore "dibenzo-[2.2.2] cryptand" was considered necessary.

The cavity size of [2.2.2] cryptand (2.8 A° in diameter) closely matches the size of potassium cation (2.66 A°).

Substituted [2.2.2] cryptands, such as dibenzo [2.2.2] cryptand, possess a guest binding site (ionophore) having heteroatom with nonbonding electron pairs such as nitrogen, capable of binding potassium ($K^+$) selectively in its cavity.

The synthesis of dibenzo-cryptand [2.2.2]; namely 4,7,13,16,20,23-hexaoxa-1,10-diaza-19(1,2),24(1,2)-dibenzabicyclo[8.8.6]tetracosaphane (VII) is outlined in Scheme 1. The commercially available 2-nitrophenol (I) was chosen as a starting material.

Treatment of two equivalents of (I) with 1,2-dibromoethane and potassium carbonate in dimethyl formamide (DMF) afforded 1,2-Bis (2-nitrophenoxy)ethane (II). Reduction of (II) with 10% Palladium-on-charcoal as the catalyst produced the amino derivative (III). The diamine (III) was reacted with 3,6-dioxaoctanedioyl dichloride (1,2-ethylene-O,O-diglycolic acid chloride) in tetrahydrofuran (THF) at high dilution conditions in tetrahydrofuran (Dietrich, B.; Lehn, J. M.; Sauvage, J. P.; Blanzat, J. Cryptates. X. Syntheses and physical properties of diazapolyoxamacrobicyclic systems. *Tetrahedron* 1973, 29, 1629) to give the lactam (IV). The lactam (IV) was reduced with Lithium Aluminum Hydride ($LiAlH_4$) in THF to give the azacrown (V) (Previously reported by de Silva, A. P.; Gunaratne, H. Q. N.; Samankumura, K. R. A. S. A new benzo-annelated cryptand and a derivative with alkali cation-sensitive fluorescence. *Tetrahedron Lett.* 1990, 31, 5193-5196). Subsequent treatment of (V) with 3,6-dioxaoctanedioyl dichloride gave (VI) which upon reduction with diborane in tetrahydrofuran (Pettit, W. A.; Iwai, Y.; Berfknecht, C. F.; Swenson, D. C. Synthesis and structure of $N^1$-e-benzo-4,7,13,16,21,26-hexaoxa-1,10-diazabicyclo[8.8.8]hexacos-23-yl-$N^2$-phenyl-thiourea. Derivative of a bifunctional complexing agent. *J. Heterocycl. Chem* 1992, 29, 877) furnished the cryptand (VII).

The phenyl groups of cryptand VII can be further derivatized by further chemical reactions such as bromination. Bromination of (VII) with 2,4,4,6-tetrabromo-2,5-cyclohexadien-1-one afforded the dibromo-cryptand (VIII).

The dibromo-cryptand (VIII) was also prepared by an alternative reaction sequence starting with azacrown (V). Bromination of (V) with bromine afforded both monobromo azacrown (IX) and dibromo azacrown (X). Treatment of (X) with 3,6-dioxaoctanedioyl dichloride afforded (XI) which upon reduction with Borane in THF gave the dibromo-cryptand (VIII). (Naguib, Y M A. *Molecules* 2009, 14, 3600-3609).

Scheme 1

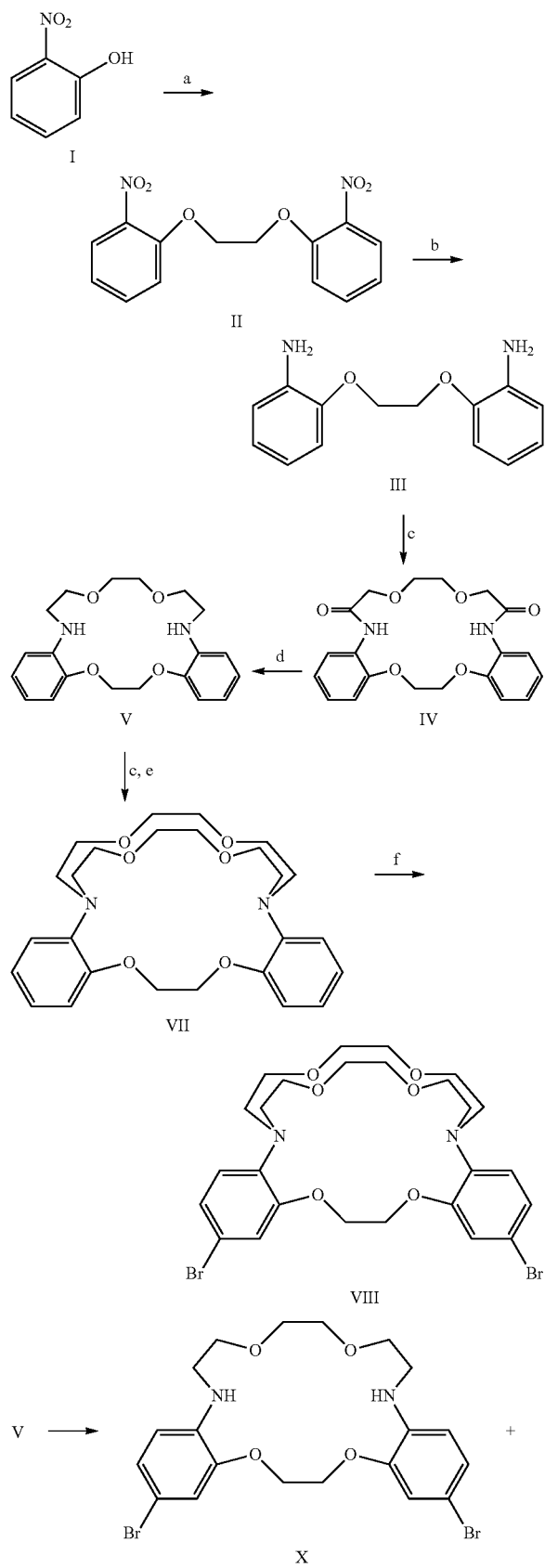

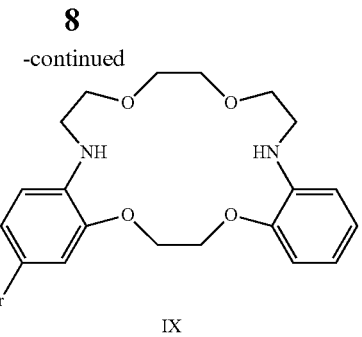

(a) BrCH$_2$CH$_2$Br, K$_2$CO$_3$; (b) 10% Pd/C;
(c) ClCOCH$_2$OCH$_2$CH$_2$OCH$_2$COCl; (d) LiAlH$_4$; (e) Borane;
(f) 2,4,4,6-Tetrabromo-2, 5-cyclohexadien-1-one Di-substituted [2.2.2] cryptand possesses a guest binding site (ionophore) having heteroatom with nonbonding electron pairs such as nitrogen, capable of binding potassium (K$^+$) selectively in its cavity.

Cryptand is a phase-transfer agent used to complex [$^{18}$F] fluoride in non-aqueous environment to form [$^{18}$F] fluoride cryptate complexes suitable for performing radio-labeling reactions to generate [$^{18}$F] fluorinated species to be viewed through an imaging agent such as Positron Emmision Tomography ("PET") and that a [$^{18}$F] fluorinated species defined herein comprises chemical or biological [$^{18}$F] fluorinated compounds for use as imaging agents.

Several approaches for incorporating $^{18}$F in biomolecules are described in the following references: Kuhnast, B., et al. (2004) J. Am. Chem. Soc., 15, 617-627; Garg, P. K., et al. (1991) Bioconj. Chem., 2, 44-49; Lee, B. C., et al. (2004) J. Am. Chem. Soc., 15, 104-111; Chen, X., et al. (2004) J. Am. Chem. Soc., 15, 41-49; Glaser, M., et al. (2004) J. Am. Chem. Soc., 15, 1447-1453; Toyokuni et al. Bioconjug. Chem. (2003) 14: 1253-9; and Couturier, O., et al. (2004) Eur. J. of Nuc. Med. and Mol. Imaging, 31, 1182-1206).

The present invention is not to be limited in scope by specific to embodiments described herein. Indeed, various modifications of the inventions in addition to those described herein will become apparent to those skilled in the art from the foregoing description. Such modifications are intended to fall within the scope of the appended claims.

Various publications and patent applications are cited herein, the disclosures of which are incorporated by reference in their entireties.

REFERENCES

Jewett et al, "Multiphase Extraction: Rapid Phase-Transfer of [18F]Fluoride Ion for Nucleophilic Radiolabeling Reactions," Appl. Radiat. Isot., vol. 39, No. 11, pp. 1109-1111, 1988

No-Carrier-Added (NCA) ARYL [$^{18}$F] Fluorides Via the Nucleophilic Aromatic Substitution of Electron-Rich Aromatic Rings," Ding et al. Journal of Fluorine Chemistry vol. 48, pp. 189-205 (1990)

The Synthesis of 6-[$^{18}$] Fluoro-L-Dopa by Chiral Catalytic Phase-Transfer Alkylation," C. Lemaire et al., J. Label Labelled Cpd., Radiopharm 42 (1999) S113-S115

F-18 labeled biomolecules for PET studies in the neurosciences, Ding Y S, Journal of Fluorine Chemistry, 101: (2) 291-295 February 2000

Proton Irradiation of [18O]02: Production of [$^{18}$F]F2 and [$^{18}$F]F2+[$^{18}$F]OF2, Allyson Bishop et al., Nuclear Med. Biol. 1996, 23, 189-199

4-[$^{18}$F]Fluoroarylalkylethers via an improved synthesis of n.c.a. 4-[$^{18}$F]fluorophenol," T. Ludwig et al., Nuclear Medicine and Biology 29 (2002) 255-262

Babb, D. A., et al., "Synthesis of Hydroxymethyl-Functionalized-Diazacrowns and Cryptands," Journal of Heterocyclic Chemistry 23:609-613 (1986)

Blasius, E., et al., "Preparation and Application of Polymers with Cyclic Polyether Anchor Groups," Pure & App. Chem. 54(11):2115-2128 (1982)

Bradshaw, J. S., et at, "Stable Silica Gel-Bound Crown Ethers. Selective Separation of Metal Ions and a Potential for Separations of Amine Enantiomers," Journal of Inclusion Phenomena and Molecular Recognition in Chemistry 7:127-136 (1989)

Bradshaw, J. S., et al., "Silical gen-bound aza-crowns for the selective removal and concentration of metal ions," Pure & Appl. Chem. 61:1619-1624 (1989)

Krakowiak, K. E., et al., "Syntheses of the Cryptands. A Short Review," Israel Journal of Chemistry 32:3-13 (1992)

Krakowiak, K. E., et al., "One-step Methods to Prepare Cryptands and Crowns Containing Reactive Functional Groups," Journal of Heterocyclic Chemistry 27:1011-1014 (1990)

Krespan, C. G., "Functionalized Macroheterobicyclic Compounds," Journal of Organic Chemistry 45:1177-1180 (1980)

Montanari, F., et al., "Hydroxymethyl Derivatives of 18-Crown-6 and [2.2.2]Cryptand: Versatile Intermediates for the Synthesis of Lipophilic and Polymer-Bonded Macrocyclic Ligands,", J. Org. Chem., 47:1298-1302 (1982)

Dietrich, B., "Cryptands," in Comprehensive Supramolecular Chemistry, Atwood et al. eds., Jean-Marie Lehn—Chairman of the Editorial Board, New York: Pergamon, 1996, vol. 1, G. W. Gokel, ed., pp. 154-157, 186, 192

What is claimed is:

1. A cryptate complex comprising potassium [$^{18}$F] fluoride and an aryl-fused [2.2.2] cryptate wherein the cryptate is

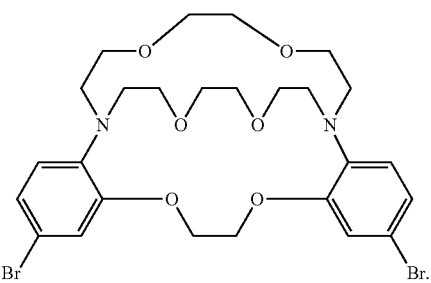 [SMILES: Brc1ccc2c(c1)OCCOc1cc(Br)ccc1N1CCOCCOCCN2CCOCCOCC1]

* * * * *